(12) United States Patent
Kang

(10) Patent No.: US 10,779,987 B2
(45) Date of Patent: Sep. 22, 2020

(54) SILVER NANO ELECTRONIC INK-PRINTED HEATING ELEMENT SEPARATION TYPE ELECTRIC THERMOTHERAPY DEVICE AND MANUFACTURING METHOD THEREFOR

(71) Applicants: PARU CO., LTD., Jeollanam-do (KR); ZIVON CO., LTD., Jeollanam-do (KR)

(72) Inventor: Moon Sig Kang, Jeollanam-do (KR)

(73) Assignees: PARU CO., LTD., Jeollanam-So (KR); ZIVON CO., LTD., Jeollanam-Do (KR)

(*) Notice: Subject to any disclaimer, the term of this patent is extended or adjusted under 35 U.S.C. 154(b) by 954 days.

(21) Appl. No.: 15/124,971

(22) PCT Filed: May 16, 2014

(86) PCT No.: PCT/KR2014/004379
§ 371 (c)(1),
(2) Date: Sep. 9, 2016

(87) PCT Pub. No.: WO2015/167063
PCT Pub. Date: Nov. 5, 2015

(65) Prior Publication Data
US 2017/0049610 A1    Feb. 23, 2017

(30) Foreign Application Priority Data
Apr. 28, 2014    (KR) .................. 10-2014-0050641

(51) Int. Cl.
*A61F 7/00*    (2006.01)
*A61F 7/08*    (2006.01)
*H05B 3/12*    (2006.01)

(52) U.S. Cl.
CPC ............ *A61F 7/007* (2013.01); *A61F 7/0097* (2013.01); *A61F 7/08* (2013.01); *H05B 3/12* (2013.01);
(Continued)

(58) Field of Classification Search
CPC ............ A61F 7/0007; A61F 2007/0074; A61F 7/0097; A61F 2007/0098; H05B 3/12;
(Continued)

(56) References Cited

U.S. PATENT DOCUMENTS

| 2005/0007406 A1* | 1/2005 | Haas | A41D 13/0051 347/17 |
| 2008/0083740 A1* | 4/2008 | Kaiserman | A43B 7/04 219/520 |
| 2011/0275981 A1* | 11/2011 | Singh | A61B 17/0231 604/20 |

FOREIGN PATENT DOCUMENTS

| CN | 200994614 Y | 12/2007 |
| CN | 201499921 U | 6/2010 |

(Continued)

OTHER PUBLICATIONS

International Search Report for PCT/KR2014/004379—dated Jan. 26, 2015.
(Continued)

*Primary Examiner* — Kaitlyn E Smith
*Assistant Examiner* — Bradford C. Blaise
(74) *Attorney, Agent, or Firm* — The PL Law Group, PLLC

(57) ABSTRACT

A silver-nano electronic-ink print heating element separation-type electric thermotherapy apparatus includes two or more silver-nano electronic-ink print heating elements that emit heat using a power source applied from a power source unit. The electric thermotherapy apparatus includes a control
(Continued)

unit which receives the power source from the power source unit to output a power source on-off signal and a temperature control signal for controlling the two or more silver-nano electronic-ink print heating elements, and the silver-nano electronic-ink print heating elements emitting heat depending on the power source and/or a temperature applied using the control unit, whereby an integral heating element, such as an electric mat, an electric mattress, an electric cushion, a hot-water mat, and an electric carpet, includes two or more divided parts, and thus it is easy to separately use the parts of the heating element and to independently control the temperature for the heating parts.

7 Claims, 8 Drawing Sheets

(52) U.S. Cl.
CPC *A61F 2007/0074* (2013.01); *H05B 2203/013* (2013.01); *H05B 2203/017* (2013.01); *H05B 2203/02* (2013.01)

(58) Field of Classification Search
CPC ........ H05B 2203/013; H05B 2203/017; H05B 2203/02
See application file for complete search history.

(56) References Cited

FOREIGN PATENT DOCUMENTS

| | | |
|---|---|---|
| EP | 1718116 A2 | 11/2006 |
| KR | 10-0819520 B1 | 4/2008 |
| KR | 10-2009-0015516 A | 2/2009 |
| KR | 10-2011-0094174 A | 8/2011 |
| KR | 10-1113713 B1 | 2/2012 |
| KR | 10-1163485 B1 | 7/2012 |
| KR | 20-2013-0002247 U | 4/2013 |
| KR | 10-1272959 B1 | 6/2013 |
| KR | 10-2013-0119692 A | 11/2013 |

OTHER PUBLICATIONS

Office action dated Jul. 18, 2017 from Japan Intellectual Property Office in a counterpart Japanese Patent Application No. 2017-502545 (all the cited references are listed in this IDS.).

Office action dated May 15, 2017 from China Patent Office in a counterpart China Patent Application No. 201480075892 (all the cited references are listed in this IDS.) (English translation is also submitted herewith.).

\* cited by examiner

SILVER NANO ELECTRONIC INK-PRINTED HEATING ELEMENT SEPARATION TYPE ELECTRIC THERMOTHERAPY DEVICE AND MANUFACTURING METHOD THEREFOR

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2014/004379, filed May 16, 2014, which claims priority to the benefit of Korean Patent Application No. 10-2014-0050641 filed in the Korean Intellectual Property Office on Apr. 28, 2014, the entire contents of which are incorporated herein by reference.

TECHNICAL FIELD

The present invention relates, in general, to an electric thermotherapy apparatus and, more particularly, to a silver-nano electronic-ink print heating element separation-type electric thermotherapy apparatus, which includes a silver-nano electronic-ink print heating element formed using a gravure device and the temperature of which is controlled by a user for respective body parts or areas, and a method of manufacturing the same.

BACKGROUND ART

Recently, technologies for mass-producing printed electronic elements at low cost have been actively developed using R2R gravure printing.

In a conventional process of manufacturing a heating film, most products are produced based on screen printing and etching processes, and most such processes are complicated and incur high manufacturing costs.

Most currently released heaters are slim and lightweight, as an alternative to conventional heavy and thick heaters. An example of the conventional heaters is disclosed in Korean Patent No. 1113713.

In the conventional art, a heating circuit is printed on one substrate using a fine printing technology, an insulating thin film is printed thereon to ensure insulation, a sensor circuit is printed on the insulating thin film to thus minimize the thickness of the resultant substrate, and a cover substrate is applied thereon.

Typical heating bedclothes other than single-person heating bedclothes have a large area. Accordingly, when a single person uses the heating bedclothes, areas other than the area occupied by a user or areas other than the area desired to be heated, corresponding in position to a specific body part, may also be heated, resulting in excessive electric consumption.

Further, since old times, lower-body bathing has been developed as an adjuvant therapy of Korean medicine, and accordingly, heating bedclothes are in the limelight. In lower-body bathing, the lower body is warmed using water to compensate for the unbalanced body temperature between the upper and lower bodies to thus remove cold energy from the body, thereby helping to improve physical functioning.

According to Sasang physical constitution typology, tae-eum and so-eum physiological type persons are encouraged to engage in lower-body bathing because their health improves when they sweat. However, lower-body bathing may be harmful to tae-yang and so-yang physiological type persons, who have a lot of hot vital energy, when they sweat during lower-body bathing. Further, most conventional heating products are manufactured using hot wires or PVC hoses, and some products on the market cause a problem of exposure to electromagnetic waves. However, bedclothes including silver-nano electronic-ink print heating elements have not yet come onto the market.

Further, the temperature of each body part depends on the physical constitution of each user, and accordingly, users may experience slight discomfort when they use a conventional integral heating member.

SUMMARY

Accordingly, the present invention has been made keeping in mind the above problems occurring in the related art, and an object of the present invention is to provide a silver-nano electronic-ink print heating element separation-type electric thermotherapy apparatus, which individually or simultaneously performs temperature control and on-off control of one or more silver-nano electronic-ink print heating elements, and a method of manufacturing the same.

Another object of the present invention is to provide a silver-nano electronic-ink print heating element separation-type electric thermotherapy apparatus, which includes a silver-nano electronic-ink print heating element manufactured using a copper foil tape or an electric wire and a laminating process for electrode connection, and a method of manufacturing the same.

A further object of the present invention is to provide a silver-nano electronic-ink print heating element separation-type electric thermotherapy apparatus, which uniformly controls the number of lines of plate-making halftone dots according to a roll-to-roll printing process using a silver-nano ink and which includes a PTC ink printed using a gravure device, and a method of manufacturing the same.

Yet another object of the present invention is to provide a silver-nano electronic-ink print heating element separation-type electric thermotherapy apparatus, which includes a self-temperature controllable PTC silver-nano electronic-ink print heating element, and a method of manufacturing the same.

In order to accomplish the above objects, the present invention provides an electric thermotherapy apparatus including two or more silver-nano electronic-ink print heating elements that emit heat using a power source applied from a power source unit. The electric thermotherapy apparatus includes a control unit which receives the power source from the power source unit to output a power source on-off signal and a temperature control signal for controlling the two or more silver-nano electronic-ink print heating elements, and the silver-nano electronic-ink print heating elements emitting heat depending on the power source and/or a temperature set using the control unit. The silver-nano electronic-ink print heating elements may be constituted by forming patterns on two or more substrates using a conductive silver ink, forming a pair of electrodes on each silver paste, and printing a PTC (positive temperature coefficient) ink for gravure on the substrates, the conductive silver ink, and the electrodes.

The silver-nano electronic-ink print heating element includes an insulator layered on an opposite surface of the substrate, a lower outer cover, including a PE (polyethylene) foam or a PI (polyurethane) foam, layered on a lower side of the insulator, a blocking fabric layered on an upper side of the silver-nano electronic-ink print heating element, and an upper outer cover layered on an upper side of the blocking fabric.

In order to accomplish the above objects, the present invention also provides a method of manufacturing a silver-nano electronic-ink print heating element separation-type electric thermotherapy apparatus. The method may include (a) forming two or more silver-nano electronic-ink print heating elements on one substrate, (b) layering an insulator on a lower outer cover, (c) layering the silver-nano electronic-ink print heating elements, formed during the step (a), on an upper side of the insulator, (d) attaching blocking fabrics to upper sides of the silver-nano electronic-ink print heating elements, and (e) layering an upper outer cover on the blocking fabrics.

Further, the step (a) includes (a-1) preparing a substrate, (a-2) forming a pattern on the substrate using a conductive silver ink according to a gravure printing process, and (a-3) printing a PTC (positive temperature coefficient) ink for gravure on the substrate and the pattern of the conductive silver ink.

The conductive silver ink may be manufactured using a step which includes manufacturing a silver-nano gel and manufacturing the conductive silver ink, including the manufactured silver-nano gel, to print the pattern through which an electric signal is applied. The PTC ink for gravure may include one or more of a polymer, carbon, and graphite.

Any one ethylene copolymer of an ethylene-acrylic acid copolymer (EAA), an ethylene-ethyl acrylate copolymer (EEA), an ethylene-vinyl acetate copolymer (EVA), an ethylene-methyl methacrylate copolymer (EMMA), an ethylene-methyl acrylate copolymer (EMA), an ethylene-methacrylic acid copolymer (EMAA), and an ethylene glycidyl methacrylate copolymer (EGMA) may be used, or any one of polyethylene (PE), polyurethane, and polyester may be used as a polymer component added to a conductive PTC ink.

Further, in the silver-nano electronic-ink print heating element separation-type electric thermotherapy apparatus, the pattern may be formed using a plate-making roller, an outer surface of which is engraved with a core cell pattern and which includes the conductive silver ink injected into the core cell pattern, a pressing roller for pressing a film moving between the plate-making and pressing rollers to transfer the pattern of the plate-making roller to one side of the film using the conductive ink, and one or more guide rollers for guiding the film.

According to the silver-nano electronic-ink print heating element separation-type electric thermotherapy apparatus and the method of manufacturing the same of the present invention, the integral heating element, such as an electric mat, an electric mattress, an electric cushion, a hot-water mat, and an electric carpet, includes two or more divided parts, and thus it is easy to separately use the parts of the heating element and to independently control the temperature for the heating parts.

Further, according to the silver-nano electronic-ink print heating element separation-type electric thermotherapy apparatus and the method of manufacturing the same of the present invention, vasodilation and muscle-relaxation effects may be obtained and blood circulation may be promoted due to a lower-body bathing function to thus help in recovery from fatigue and increase the body temperature, thereby increasing the blood flow. Accordingly, blood circulation and metabolism are promoted and waste discharge is assisted. Therefore, the electric thermotherapy apparatus may be applied to and combined with medical or heating products, depending on various circumstances and applications in many ways.

Further, according to the silver-nano electronic-ink print heating element separation-type electric thermotherapy apparatus and the method of manufacturing the same of the present invention, the number of lines and the depth of roll plate-making halftone dots may be controlled to obtain a desired resistance value in a desired area. Accordingly, the heating temperature may be controlled depending on the corresponding resistance value.

Further, according to the silver-nano electronic-ink print heating element separation-type electric thermotherapy apparatus and the method of manufacturing the same of the present invention, since an R2R gravure printing process is used in place of a screen printing process, which is used as a process of manufacturing a conventional PTC planar heating element, the manufacturing process may be simplified and a cost-saving effect may be obtained.

In addition, according to the silver-nano electronic-ink print heating element separation-type electric thermotherapy apparatus and the method of manufacturing the same of the present invention, the electric current change of the PTC silver-nano electronic-ink print heating element exceeds 50% depending on the temperature. Therefore, an instantaneous heating temperature is high at low temperatures and a low electric current is maintained at high temperatures, thereby reducing the risk of fire and ensuring high thermal efficiency at a low electric power.

DETAILED DESCRIPTION

The terms or words used in the present specification and the claims should not be construed to be limited to the typical or dictionary meanings, but to be understood as having meanings and concepts corresponding to the technical spirit of the present invention based on the principle that the inventor can properly define the concept of terms to describe his own invention in the best way.

In the specification, when any portion "includes" any component, this means that the portion does not exclude other components but may further include other components unless otherwise stated. Further, the terms " . . . member", " . . . group", "module", and "device" used in the specification mean a unit that processes at least one function or operation, and may be implemented as a combination of hardware and/or software.

In each step, identification symbols (for example, a, b, c, . . . ) are not intended to describe the order of steps but are used for convenience of description, and the steps may be performed in an order different from the described order unless the specified order is clearly stated in context. That is, the steps may performed in the described order, substantially at the same time, or in reverse order to the described order.

Hereinafter, a description will be given of an embodiment of the present invention, with reference to the drawings.

Figure 1:
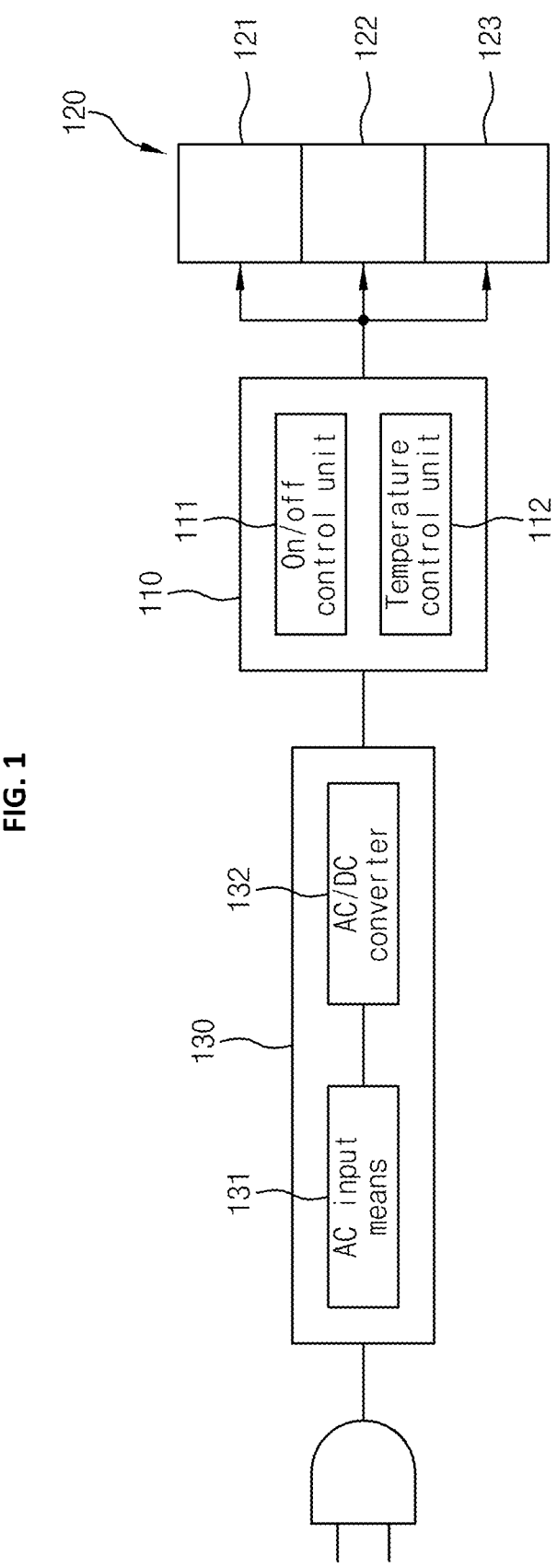
FIG. 1 is a view showing the main constitution of a silver-nano electronic-ink print heating element separation-type electric thermotherapy apparatus according to an embodiment of the present invention.
Figure 2:
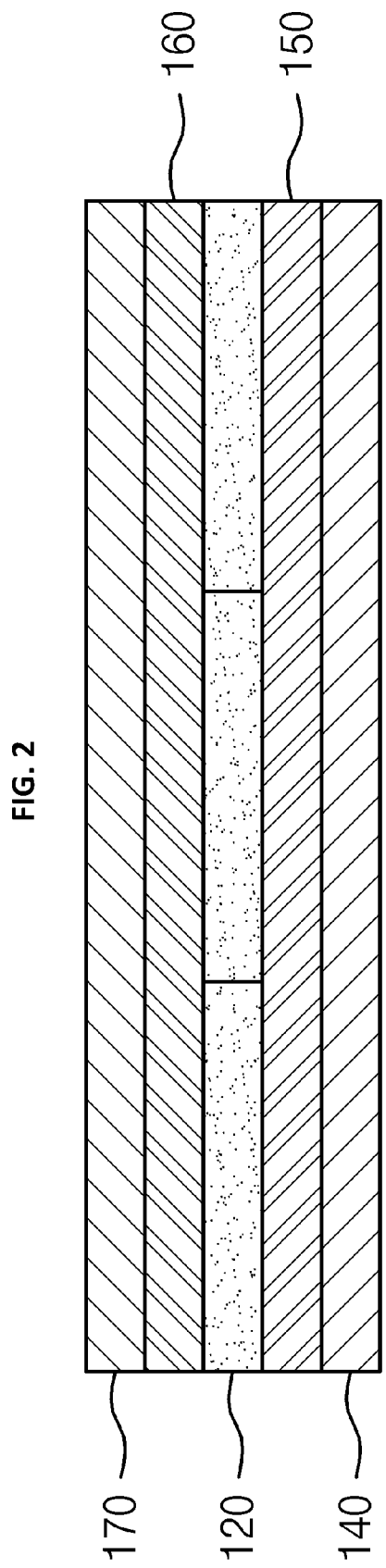
FIG. 2 is a sectional view of the silver-nano electronic-ink print heating element separation-type electric thermotherapy apparatus according to the embodiment of the present invention.
Figure 3:
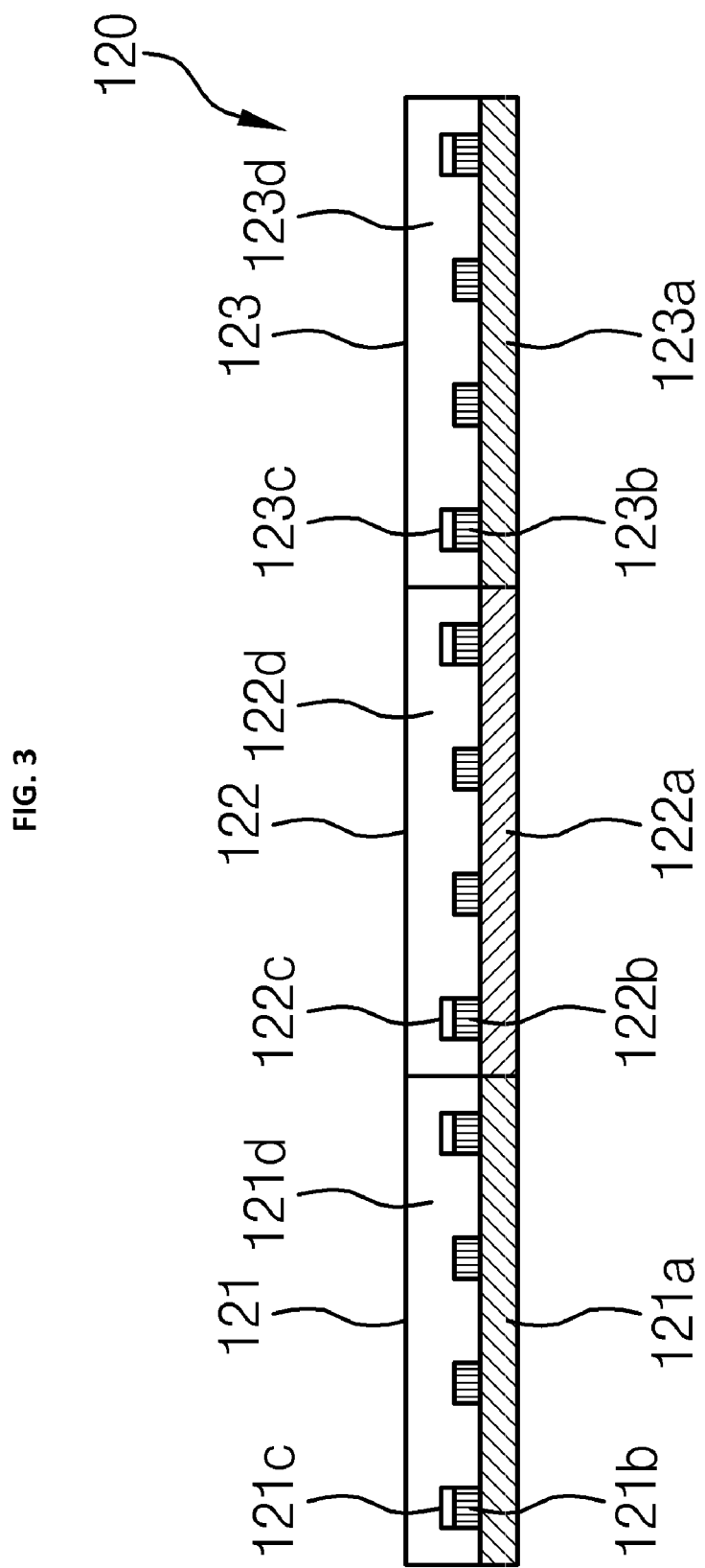
FIG. 3 is a detailed sectional view of a silver-nano electronic-ink print heating element of the present invention.

FIG. 1 is a view showing the main constitution of a silver-nano electronic-ink print heating element separation-type electric thermotherapy apparatus according to an embodiment of the present invention, FIG. 2 is a sectional view of the silver-nano electronic-ink print heating element separation-type electric thermotherapy apparatus according to the embodiment of the present invention, and FIG. 3 is a detailed sectional view of a silver-nano electronic-ink print heating element of the present invention.

As shown in the drawings, the silver-nano electronic-ink print heating element separation-type electric thermotherapy apparatus of the present invention may include a power source unit 130 for converting an external power source into a driving power source to output the driving power source, a control unit 110 for controlling the power source and the temperature of each silver-nano electronic-ink print heating element using the power source applied from the power source unit 130, and a silver-nano electronic-ink print heating element 120, which emits heat using the power source.

The present invention discloses that an alternating-current power source is not used but a direct-current power source is used as the power source unit of the silver-nano electronic-ink print heating element in order to effectively suppress electromagnetic waves, but the present invention is not limited thereto. An alternating-current or direct-current power source may be used as necessary.

The power source unit 130 includes an AC input means 131, for inputting the external alternating-current power source applied through a socket, and an AC/DC converter 132, for converting the alternating-current power source, applied from the AC input means 131, into direct current. The direct-current power source may be output from the AC/DC converter 132 to the silver-nano electronic-ink print heating element 120.

In the present invention, the direct-current conversion means is provided in the power source unit 130 to enable the silver-nano electronic-ink print heating element 120 to emit heat using the direct-current. Typically, the quantity of electromagnetic waves emitted from the heating mat is larger in the application of the alternating-current power source than in the application of the direct-current power source.

The control unit 110 supplies the power source from the power source unit 130 to silver-nano electronic-ink print heating elements 121, 122, and 123, and controls the temperature of each silver-nano electronic-ink print heating element.

For control, the control unit 110 may include an on-off control unit 111 for turning on and off the power source of each silver-nano electronic-ink print heating element and a temperature control unit 112 for controlling the temperature of each silver-nano electronic-ink print heating element on a typical control pad.

In the embodiment of the present invention, a constitution including three silver-nano electronic-ink print heating elements is exemplified.

Referring to FIG. 2, the silver-nano electronic-ink print heating element separation-type electric thermotherapy apparatus has a structure in which an insulator 150 is layered on a lower outer cover 140, the silver-nano electronic-ink print heating element 120 is provided on the insulator, a blocking fabric 160 is layered on the silver-nano electronic-ink print heating element 120, and an upper outer cover 170 is layered thereon.

It is preferable that the lower outer cover 140 include a PE (polyethylene) foam or a PU (polyurethane) foam as a buffer material and that an aluminum insulator be used as the insulator 150.

A TPU electromagnetic-wave blocking film or a magnetic-field blocking sheet may be used as the blocking fabric 160.

A TPU film is laminated with an LDPE (low-density polyethylene) film laminated with a carbon non-woven fabric to manufacture the TPU (thermoplastic polyurethane) electromagnetic-wave blocking film. The TPU electromagnetic-wave blocking film blocks electromagnetic waves and provides a sense of comfort.

The LDPE film layer is layered on the carbon non-woven fabric made of a fibrous material, and the TPU film is laminated thereon using an extruding machine to manufacture the TPU electromagnetic-wave blocking film.

The LDPE (low density polyethylene) is manufactured using a high-pressure radical polymerization process, thus having many long branched chains. Accordingly, impact resistance, low-temperature bromination resistance, flexibility, processability, transparency of the film, chemical resistance, water resistance, and electric insulation are excellent.

A permalloy layer may be layered on the upper side of the TPU electromagnetic-wave blocking film to more effectively block a magnetic field.

Permalloy is an alloy including about 80% nickel and 20% iron, and is an excellent magnetic material having very high permeability and low magnetic hysteresis loss. Permalloy has high processability and is thus easily processed into various complicated forms.

Further, when a wall is built using permalloy, external electromagnetic radiation cannot penetrate the wall because it is absorbed by the wall. Further, when the permalloy wall covers an area of generation of a magnetic field, the magnetic field cannot be emitted to the outside.

In addition, a flooring material such as Monoleum may be used as the upper outer cover 170.

In the above, the upper outer cover 170 is layered on the blocking fabric 160. However, the blocking fabric 160 and the upper outer cover 170 may not be separately used, but the upper outer cover may be used while being laminated with the carbon non-woven fabric having the blocking function.

The silver-nano electronic-ink print heating element 120 consists of three parts and is layered on the insulator 150. The power sources and the temperatures of the silver-nano electronic-ink print heating elements are controlled by the control unit 110.

For control, in the silver-nano electronic-ink print heating elements, the patterns of the silver paste 121*b*, 122*b*, and 123*b* are formed on respective substrates 121*a*, 122*a*, and 123*a*, and a pair of electrodes 121*c*, 122*c*, and 123*c* is formed on the silver paste.

That is, a pair of electrodes may be formed in each silver-nano electronic-ink print heating element to supply the power source.

More specifically, in the silver-nano electronic-ink print heating element of the present invention, the patterns are gravure-printed on the substrates 121a, 122a, and 123a using the conductive silver-nano inks 121b, 122b, and 123, the electrodes 121c, 122c, and 123c are formed on the patterns, and PTC (positive temperature coefficient) inks for gravure 121d, 122d, and 123d are printed on a portion of the substrates, the conductive silver inks 121b, 122b, and 123, and the electrodes 121c, 122c, and 123c.

Hereinafter, a method of manufacturing the silver-nano electronic-ink print heating element separation-type electric thermotherapy apparatus having the aforementioned constitution will be described with reference to the drawings.

Figure 4:
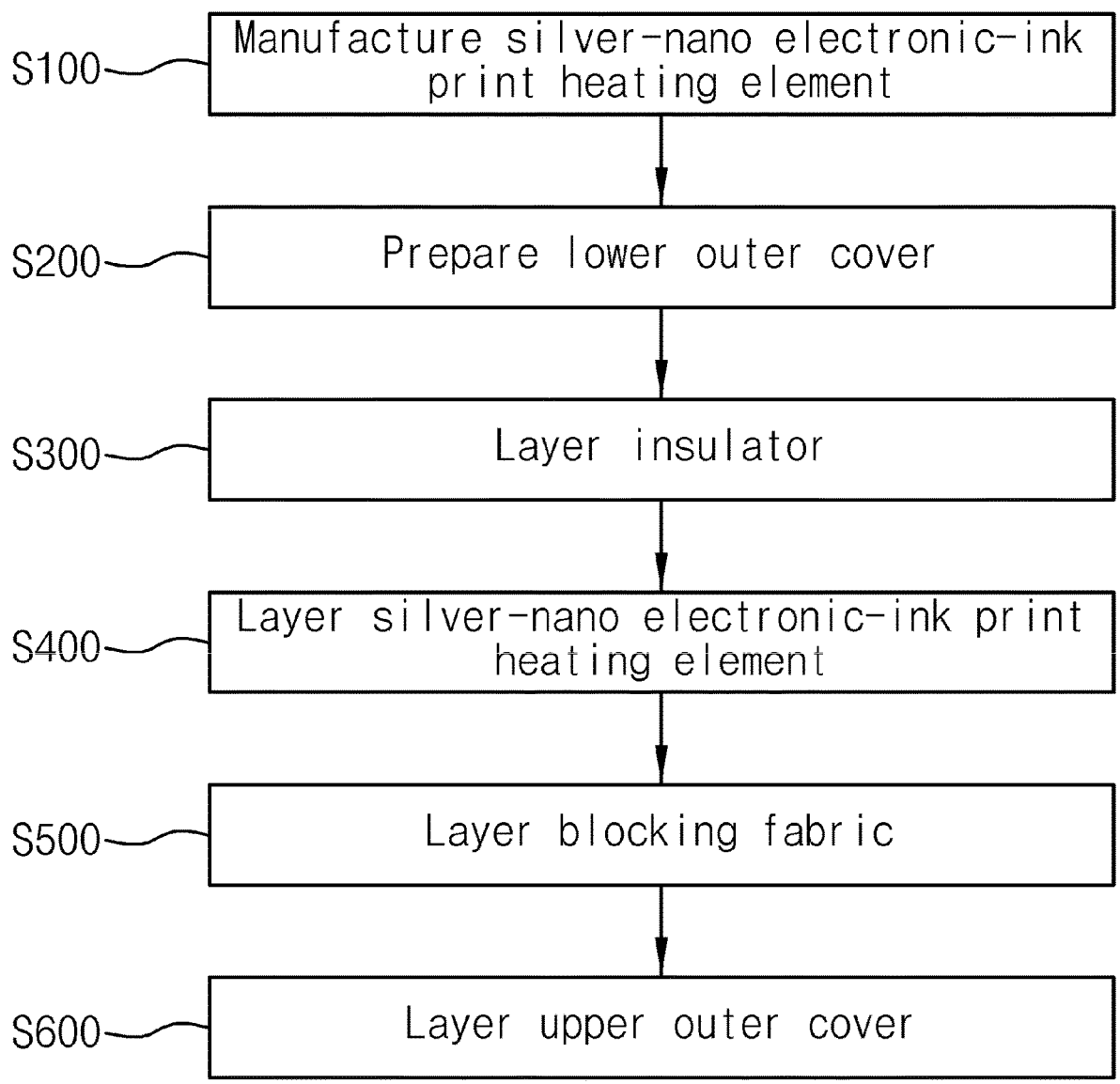
FIG. 4 is a flowchart showing a method of manufacturing a silver-nano electronic-ink print heating element separation-type electric thermotherapy apparatus according to the embodiment of the present invention.

FIG. 4 is a flowchart showing the method of manufacturing the silver-nano electronic-ink print heating element separation-type electric thermotherapy apparatus according to the embodiment of the present invention. First, the silver-nano electronic-ink print heating element 120 is manufactured (S100), and the insulator 150 is then attached to the prepared lower outer cover 140 using a conductive adhesive (S200 to S300).

Subsequently, the silver-nano electronic-ink print heating element 120, manufactured during the step S100, may be layered on the insulator 150 and attached thereto (S400), the blocking fabric 160 may be layered on the upper side of the silver-nano electronic-ink print heating element 120 (S500), and the upper outer cover 170 may be layered thereon, thereby manufacturing the electric thermotherapy apparatus (S600).

The upper outer cover laminated with the carbon nonwoven fabric may be layered on the upper side of the silver-nano electronic-ink print heating element 120 without the two steps S500 and S600.

In order to manufacture the silver-nano electronic-ink print heating element of the present invention, the silver-nano gel is first manufactured (S110).

The silver-nano gel of the present invention may be a conductive silver-nano gel formed using a gravure device.

A detailed description thereof will be given with reference to the drawings.

Figure 5:
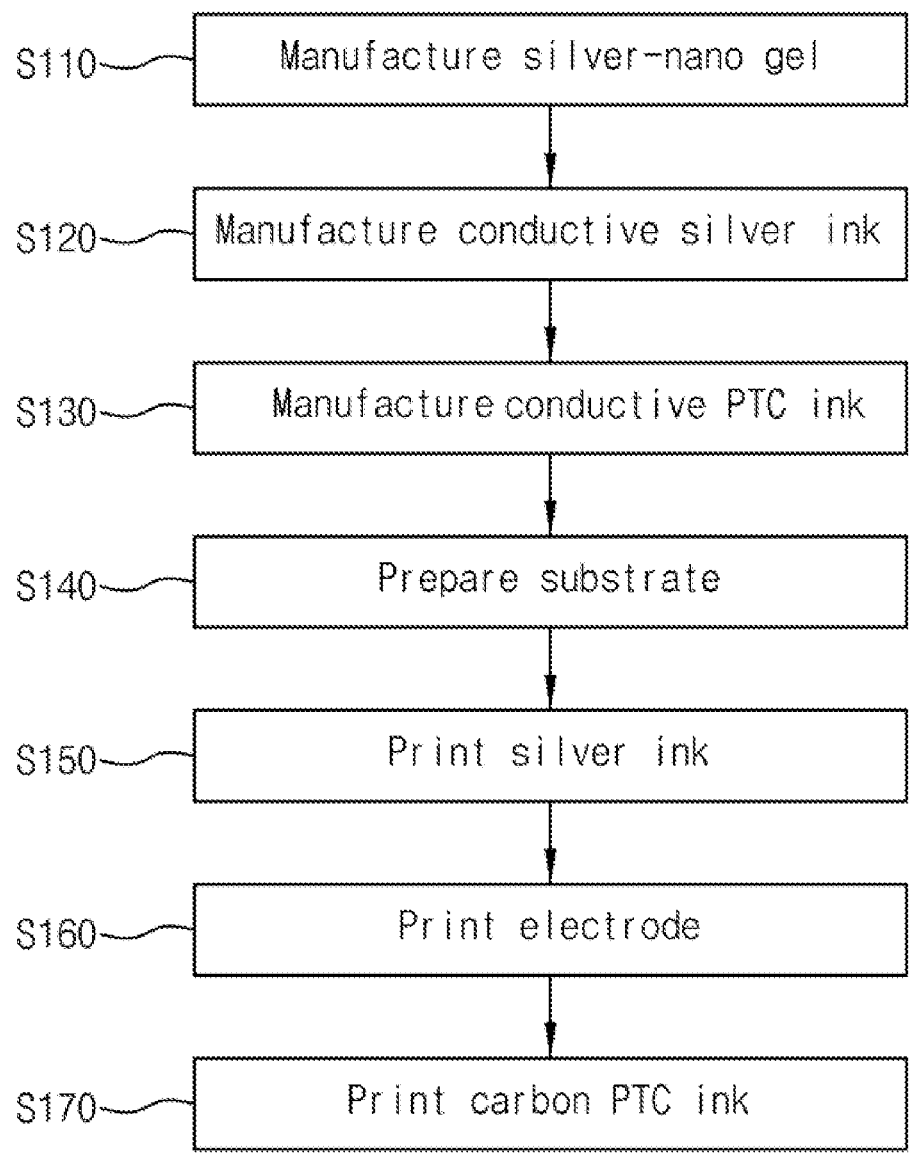
FIG. 5 is a flowchart showing the manufacture of a planar heating element.
Figure 6:
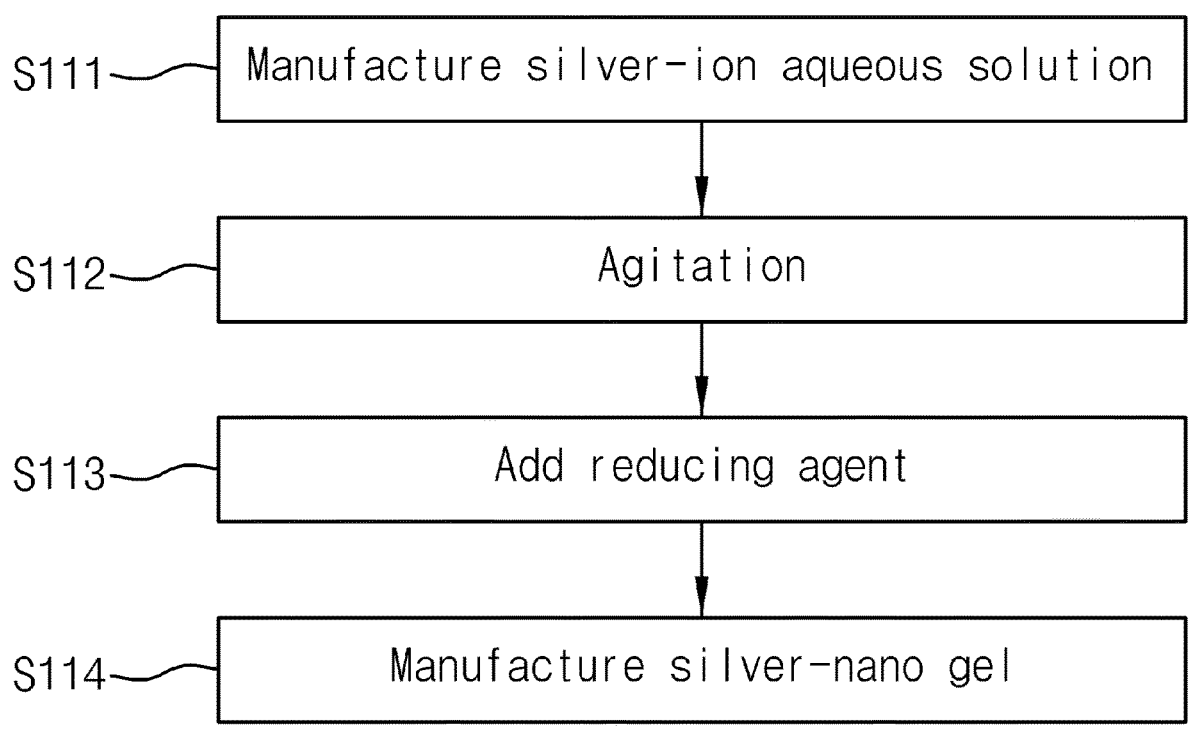
FIG. 6 is a flowchart specifically showing the generation of a silver-nano gel.

FIG. 5 is a flowchart showing the formation of the silver-nano gel, and 0.3 g of $AgNO_3$ is dissolved in 10 ml of distilled water to manufacture a silver-ion aqueous solution (S111).

That is, 0.3 g of silver oxide ($AgNO_3$) including silver (Ag) having a nano-particle size and nitrate ($NO_3$) mixed therein is dissolved in 10 ml of distilled water to manufacture the silver-ion aqueous solution.

In the present invention, the silver oxide is dissolved in distilled water to manufacture the silver-ion aqueous solution. However, a silver-oxide ($CH_3COOAg$) aqueous solution including silver (Ag) having a nano-particle size and acetic acid ($CH_3COO$) may be dissolved in distilled water to manufacture the silver-ion aqueous solution.

One or more polymer binders selected from polymer pyrrolidone, polymer urethane, and polymer amide groups are added to the silver-ion aqueous solution, manufactured during the step S111, and a dispersing agent is added so as to ensure uniform dispersion, followed by agitation (S112).

In the present invention, for convenience of description, 0.02 g of polymer pyrrolidone (having a number average molecular weight of 50,000) is added to the silver-ion aqueous solution and agitated using a homogenizer so as to ensure uniform dispersion.

0.5 g of a 10% hydrazine ($N_2H_4$) aqueous solution is slowly added to the solution dispersed during the step S112, and further agitated for 3 hours to manufacture a dark green solution during the step S113.

Hydrazine ($N_2H_4$) acts as a reducing agent. Naturally, in addition to hydrazine, one or more reducing agents selected from the group consisting of sodium borohydride ($NaBH_4$), formaldehyde, an amine compound, a glycol compound, glycerol, dimethyl formamide, a tannic acid, citrate, and glucose may be added.

0.1 g of diethanol 2,2-azobis is added to a silver precipitate, which is obtained by adding 20 ml of acetone to the solution manufactured during the step S113 and performing agitation for 1 min and separation using a centrifuge at 6000 rpm for 30 min, thus manufacturing 0.2 g of the silver-nano gel (S114).

Diethanol 2,2-azobis is used as a stabilizing means, and is added to the silver-nano precipitate precipitated on the bottom during the agitation step, thereby performing stabilization.

Thereby, the conductive paste including the silver-nano gel is manufactured.

The formed conductive silver-nano particles are photographed using an electron microscope (SEM, scanning electron microscope), and the silver-nano gel particles are 10 to 100 nm in size.

After the silver-nano gel is manufactured during the step S110, the conductive silver ink including the silver-nano gel is manufactured (S120).

The conductive paste including the silver-nano gel is dispersed in a solvent at room temperature, and epoxy, silver particles, and a curing agent are added thereto and agitated to finally manufacture the conductive ink including the silver-nano gel.

More specifically, 1 wt % of the silver-nano gel, manufactured by dispersing the nano gel (100 g) of Preparation Example 1 at room temperature in ethylene glycol (20 g) for 1 hour, 13 wt % of an epoxy resin (Mw: 50,000), 84 wt % of the silver particles, and 2 wt % of the curing agent are added and agitated at room temperature for 3 hours or more, thereby manufacturing the conductive silver paste including the silver-nano gel.

In order to control the viscosity, the amount of ethylene glycol that is added is controlled to thus manufacture inks having viscosities of 200 cp and 500 cp.

Preparation Example 1

0.01 to 0.001 g/ml of diethanol 2,2-azobis was added to a precipitate, which was obtained by adding 0.1 to 0.05 g/ml of a polymer binder and 0.01 to 0.05 g/ml of a reducing agent to a silver-ion aqueous solution, performing agitation for 30 min to 3 hours, adding 10 g/ml of acetone, and performing treatment using a centrifuge at 6000 rpm for 2 hours, thereby obtaining the silver-nano gel of Example 1.

The content of the polymer binder is preferably controlled to 0.01 to 0.03 wt % after centrifugation during the manufacture of the silver-nano gel of Example 1. The reason is that when the content of the polymer binder is more or less than 0.01 to 0.03 wt %, the nano gel is not formed and the silver-nano particles are not dispersed, but undergo phase separation.

Further, 1 to 0.01 g/ml of the silver-nano gel, a polar organic solvent, and 0.01 to 0.06 g/ml of any one selected from an organic additive, hexyl alcohol, dodecyl alcohol, diethylene alcohol amine, and ethylene glycol are added to manufacture the conductive ink including the silver-nano gel of Example 1, and the conductive ink is useful to be supplied to the plate-making roller 10 to thus print the core cell.

Preparation Example 2

30 g of $AgNO_3$ was dissolved in 1000 ml of distilled water to manufacture a silver-ion aqueous solution. 20 g of polymer pyrrolidone (average molecular weight of 50,000) was added to the solution, and 15 g of a hydrazine aqueous solution was slowly added thereto and agitated to manufacture a dark green solution. 2000 ml of acetone was added to the obtained solution and further agitated for 1 min, and hydroxy ethyl cellulose was added to a precipitate separated using a centrifuge at 6000 rpm for 10 min to thus manufacture 15 g of a silver-nano gel.

1 to 0.01 g/ml, and preferably 0.5 to 0.03 g/ml, of the obtained silver-nano gel, an aqueous solution or a polar organic solvent, and 0.01 to 0.06 g/ml of any one selected from an organic additive, hexyl alcohol, dodecyl alcohol, diethylene alcohol amine, and ethylene glycol were added to manufacture the conductive ink.

The resistance values were compared in Comparative Examples 1 to 5, in which the amounts of hydroxy ethyl cellulose varied based on the amount of the silver-nano gel of Example 2.

Comparative Example 1

Hydroxy ethyl cellulose was added in an amount of 0 parts by weight based on the amount of the silver-nano gel in Preparation Example 2. In addition, after the silver-nano gels obtained in the Preparation Examples were mixed with a water-soluble solvent, patterns were printed using an inkjet or gravure printing process and cured for 0 to 5 min.

Comparative Example 2

Hydroxy ethyl cellulose was added in an amount of 0.2 parts by weight based on the amount of the silver-nano gel in Preparation Example 2. After the silver-nano gels obtained in the Preparation Examples were mixed with a water-soluble solvent, patterns were printed using an inkjet or gravure printing process and cured for 0 to 5 min.

Example 3

Hydroxy ethyl cellulose was added in an amount of 0.3 parts by weight based on the amount of the silver-nano gel in Preparation Example 2. In addition, after the silver-nano gels obtained in the Preparation Examples were mixed with a water-soluble solvent, patterns were printed using an inkjet or gravure printing process and cured for 0 to 5 min.

Example 4

Hydroxy ethyl cellulose was added in an amount of 0.4 parts by weight based on the amount of the silver-nano gel in Preparation Example 2. In addition, after the silver-nano gels obtained in the Preparation Examples were mixed with a water-soluble solvent, patterns were printed using an inkjet or gravure printing process and cured for 0 to 5 min.

Example 5

Hydroxy ethyl cellulose was added in an amount of 0.5 parts by weight based on the amount of the silver-nano gel in Preparation Example 2. In addition, after the silver-nano gels obtained in the Preparation Examples were mixed with a water-soluble solvent, patterns were printed using an inkjet or gravure printing process and cured for 0 to 5 min.

Figure 8:
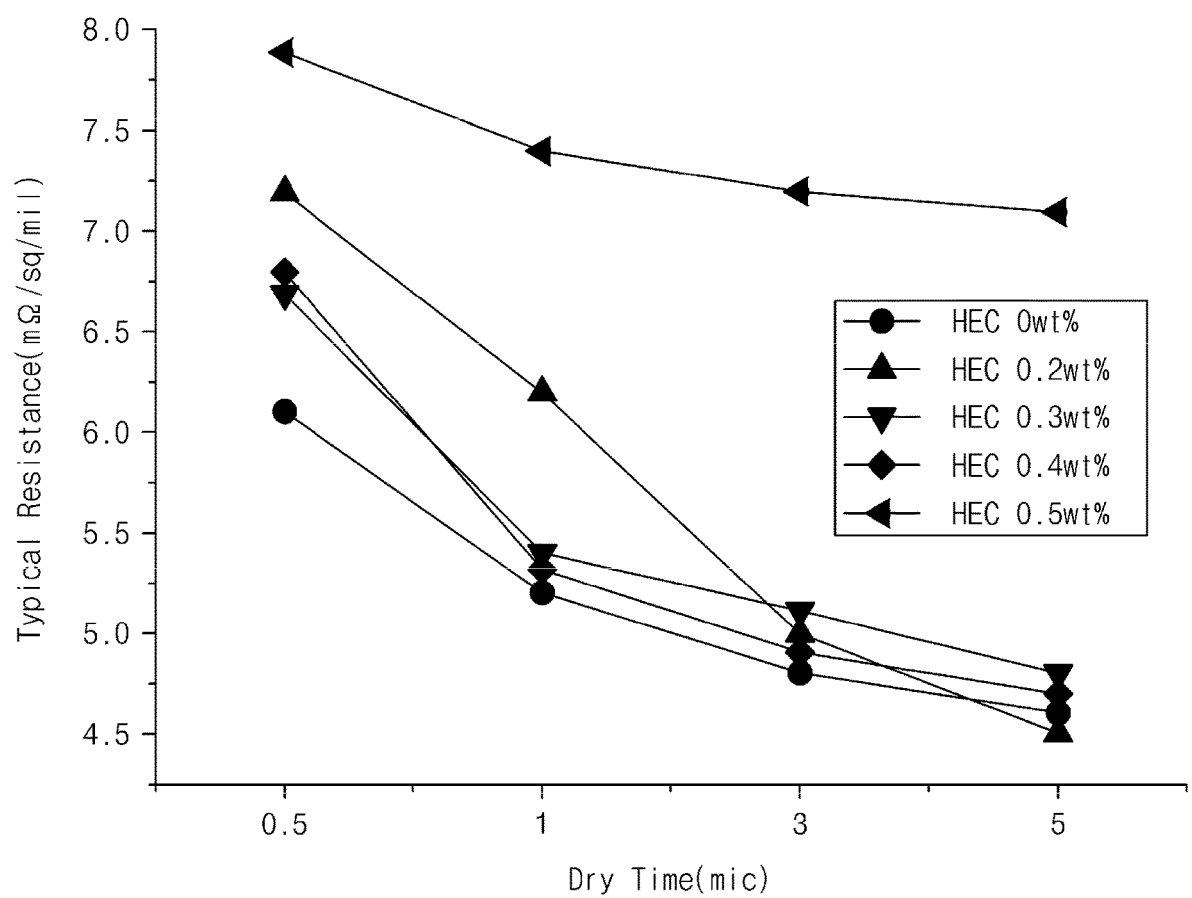
FIG. 8 is a graph obtained by measuring the resistance of the silver-nano gel of Example 2.

FIG. 8 is a graph obtained by measuring the resistance of the silver-nano gel of Example 2. Table 1 shows the result of measurement of the resistance value, the adhesion strength, and the specific resistance after the pattern is immersed in distilled water and brine and then drawn in Comparative Examples 1 to 5.

TABLE 1

| | | Curing | | | | | |
|---|---|---|---|---|---|---|---|
| | | Curing at 150° C. for 30 sec | | Curing at 150° C. for 3 min | | Curing at 150° C. for 5 min | |
| Amount | | | | Precipitated solution | | | |
| of added additive | | Distilled water 20H | Brine 20H | Distilled water 20H | Brine 20H | Distilled water 20H | Brine 20H |
| HEC 0.0 wt % | Specific resistance | 7.6 -> X | 7.7 -> X | 5.7 -> 3.1 | 5.8 -> X | 5.6 -> 4.1 | 5.6 -> X |
| | Adhesion strength | 0/100 | 0/100 | 0/100 | 0/100 | 45/100 | 0/100 |
| HEC 0.2 wt % | Specific resistance | 7.6 -> 2.3 | 4.7 -> 3.2 | 4.6 -> 2.8 | 4.7 -> 3.2 | 4.8 -> 3.3 | 4.8 -> 3.3 |
| | Adhesion strength | 0/100 | 75/100 | 69/100 | 88/100 | 95/100 | 100/100 |
| HEC 0.3 wt % | Specific resistance | 7.6 -> 3.8 | 7.7 -> 4.8 | 6 -> 4.2 | 5.8 -> 4.9 | 5.8 -> 4.9 | 5.8 -> 3.7 |
| | Adhesion strength | 32/100 | 100/100 | 100/100 | 100/100 | 100/100 | 100/100 |
| HEC 0.4 wt % | Specific resistance | 6.8 -> 2.8 | 6.2 -> 3.7 | 5.2 -> 3.2 | 5.1 -> 3.2 | 4.9 -> 3.7 | 4.9 -> 3.1 |
| | Adhesion strength | 100/100 | 100/100 | 100/100 | 100/100 | 100/100 | 100/100 |
| HEC 0.5 wt % | Specific resistance | 8.0 -> 5.0 | 8.2 -> 5.7 | 6.9 -> 5.2 | 7.4 -> 5.3 | 7.2 -> 5.8 | 7.2 -> 5.2 |
| | Adhesion strength | 100/100 | 100/100 | 100/100 | 100/100 | 100/100 | 100/100 |

Referring to FIG. 8 and Table 1, when the pattern printed using the ink, including the manufacturing composition containing 0 parts by weight (wt %) of hydroxy ethyl cellulose of Example 1, was cured for 5 min, the resistance of the pattern was stabilized from 5.6 mΩ/sq/mil to 4.1 mΩ/sq/mil in the case where the pattern was immersed in distilled water. However, the resistance of the pattern was not measured at all in the case where the pattern was immersed in brine, and accordingly the conclusion that stabilization was not ensured could be drawn.

On the other hand, in Example 5, including hydroxy ethyl cellulose in an amount of 0.5 parts by weight (wt %), both resistance values of the pattern were high when measured in the case where the pattern was immersed in distilled water and brine. Accordingly, the composition of Example 5 was judged to be unsuitable.

However, in Examples 2 to 4, the manufacturing composition included hydroxy ethyl cellulose in an amount of 0.2 to 0.4 parts by weight based on the amount of the silver-nano gel, and both resistance values of the pattern were 5 mΩ/sq/mil when measured in the case where the pattern was immersed in distilled water and brine. Accordingly, the compositions of Examples 2 to 4 could be judged to be acceptable.

Therefore, in Example 2, it is preferable that the silver-nano gel include 0.2 to 0.4 parts by weight of hydroxy ethyl cellulose based on the amount of the silver-nano gel.

After the conductive silver ink is manufactured through steps S110 to S120, a conductive PTC (Positive Temperature Coefficient) ink including a polymer, carbon, and graphite is manufactured during step S130.

When the PTC ink is manufactured during step S130, the PTC ink must be mass-produced, and the degree of deformation (distortion, bending, curling, or the like) after drying must be controlled.

Specifically, in order to manufacture the conductive paste including the polymer, carbon, and graphite, 10 to 50 wt % of the polymer was agitated in 10 to 50 wt % of a solvent at room temperature using an agitator at 2000 rpm for 1 hour, and 1 to 10 wt % of carbon and 1 to 10% of graphite were added thereto and further agitated for 1 hour to manufacture a paste. The manufactured paste was mixed using a homomixer at 2000 rpm for 10 min.

Subsequently, three roll mills were used to manufacture the PTC conductive paste. In order to control the viscosity, the amounts of added polymer, solvent, graphite, and carbon were controlled to thus manufacture inks having viscosities of 200 cp and 2,000 cp.

The amounts of the polymer, the solvent, carbon, and graphite must be freely changeable depending on the size and the pattern shape of the heating element.

The reason why the content of the ink must be changed depending on the size and the pattern of the heating element is that the resistance of the ink must be changed in order to obtain a desired temperature for a particular heating area.

Further, when a large heating element is manufactured, the heating temperature depends on the voltage applied thereto, but the resistance of the ink needs to be freely reduced or increased in order to adjust the temperature to a desired value.

The following Table 2 shows resistance value data depending on the content of the ink.

TABLE 2

| Polymer | Solvent | Carbon | Graphite | Resistance |
|---------|---------|--------|----------|------------|
| 40%     | 40%     | 15%    | 5%       | 10 Ω       |
| 45%     | 45%     | 5%     | 5%       | 150 Ω      |
| 45%     | 40%     | 10%    | 5%       | 55 Ω       |
| 40%     | 45%     | 5%     | 10%      | 25 Ω       |
| 50%     | 40%     | 5%     | 5%       | 120 Ω      |

From Table 2, it can be seen that the resistance value can be controlled only when the amounts of the polymer, the solvent, carbon, and graphite are freely changed depending on the size and the pattern shape of the heating element.

Preferable constitutional ratios after the tests are described in Table 3.

TABLE 3

| Polymer | Solvent | Carbon | Graphite | Density | Viscosity |
|---------|---------|--------|----------|---------|-----------|
| 10 to 50% | 10 to 50% | 1 to 10% | 1 to 10% | 1 to 1.2 g/ml | 200 to 2000 cp |

Generally, an ethylene copolymer, such as an ethylene-acrylic acid copolymer (EAA), an ethylene-ethyl acrylate copolymer (EEA), an ethylene-vinyl acetate copolymer (EVA), an ethylene-methyl methacrylate copolymer (EMMA), an ethylene-methyl acrylate copolymer (EMA), an ethylene-methacrylic acid copolymer (EMAA), and an ethylene glycidyl methacrylate copolymer (EGMA), may be used, or polyethylene (PE), polyurethane, or polyester may be used as the polymer component.

In the present invention, since a water-soluble PTC ink is manufactured/developed, any solvent may be used, as long as the solvent has solubility with respect to water.

In the self-temperature controllable PTC silver-nano electronic-ink print heating element of the present invention, the silver-nano ink and the carbon PTC ink are applied on the substrate using a gravure device. First, the substrate including PET or PI is prepared (S140).

The silver-nano ink is applied on the substrate, prepared during the step S140, using gravure printing (S150), the electrode is printed (S160), and the carbon PTC ink is applied to manufacture the silver-nano electronic-ink print heating element (S170).

The electrode may be formed on the silver paste using a copper foil tape or an electric wire and a laminating process during the step S160.

Figure 7:
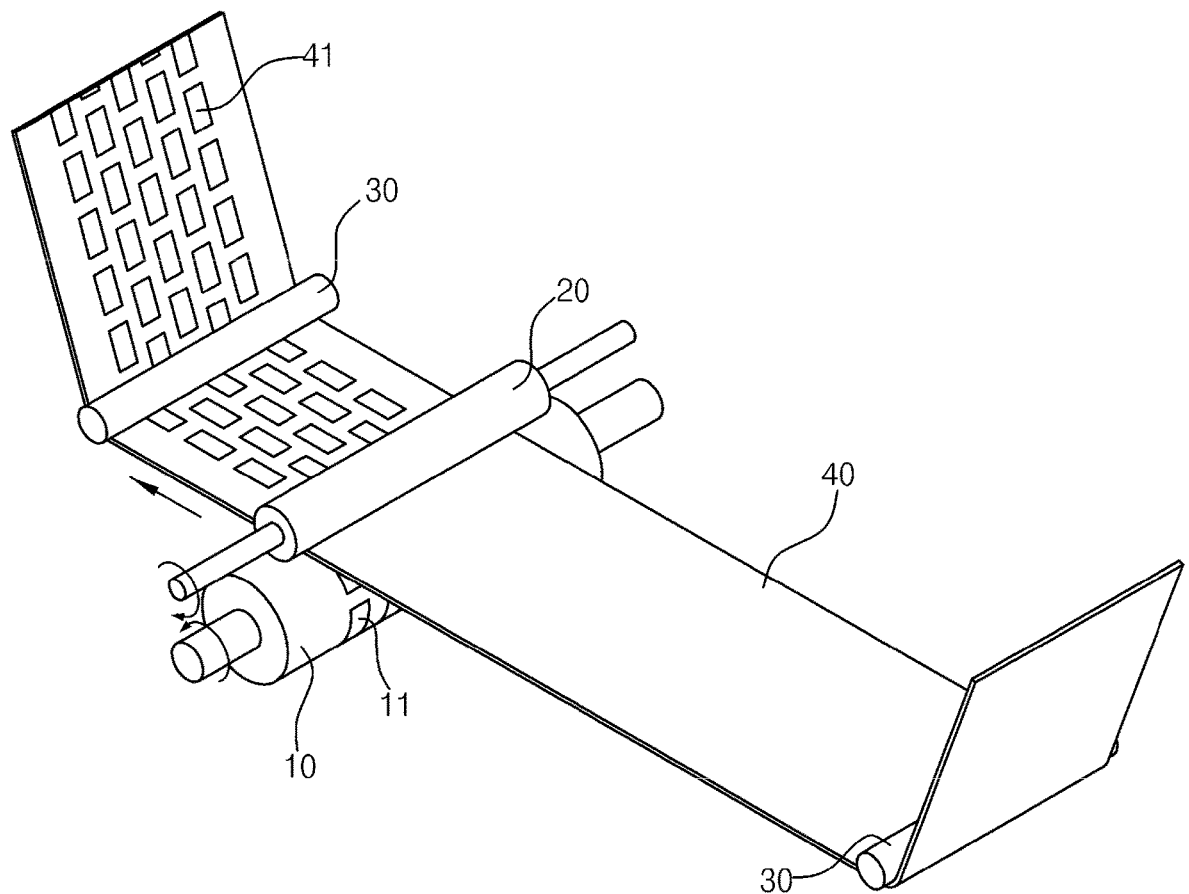
FIG. 7 is a view showing a device for manufacturing a core cell using a conductive ink according to the present invention.

FIG. 7 shows a roll-to-roll gravure printing device as an example for illustrating the present invention.

The gravure printing device includes a plate-making roller 10 having a core cell pattern 11, a pressing roller 20 for pressing a film 40 moving between the plate-making roller 10 and the pressing roller, and one or more guide rollers 30 for guiding the film 40.

The plate-making roller includes a plurality of protrusion patterns upwardly protruding to form halftone dots of the core cell, and a plurality of pattern grooves engraved between the protrusion patterns. The protrusion patterns and the pattern grooves are patterned to form a limited number of halftone dots in a predetermined area.

The pressing roller 20 comes into contact with the plate-making roller and rotates while the film 40 is interposed therebetween to thus apply the conductive ink in the pattern grooves, formed in the plate-making roller, onto the film 40, thereby transferring the pattern onto the film 40.

Preparation Example 1 of Planar Heating Element

For optimum gravure printing conditions for application of the conductive silver-nano ink and the PTC carbon ink, in order to manufacture the PTC planar heating element of the present invention, it is most preferable that the printing temperature be 150° C. or less, the printing speed be 5 to 40 m/min, the printing pressure be 20 to 40 kgf/cm$^2$, and the tension of a film be maintained at 5 to 10 kgf/cm$^2$ in order to form a core cell. The printing speed means the moving speed of the film according to the rotation of the roll during gravure printing. The printing pressure is the pressure between the pattern roll and the pressing roll of the gravure printing device, and the tension of the film means the force that is applied in order to draw the film from both ends.

When an experiment is performed while the plate-making depth is fixed to 10 um, it can be seen that many fine holes are formed in the case of 50 lines but that few fine holes are formed in the case of 150 lines. Accordingly, the number of lines may be controlled in order to control the resistance of the ink. When the plate-making depth is large, the amount of the transferred ink is increased to thus reduce the resistance of the pattern. When the depth is small, the resistance is increased.

Further, the electric current change of the PTC silver-nano electronic-ink print heating element exceeds 50%. Therefore, the instantaneous heating temperature may be high at low temperatures and a low electric current may be maintained at high temperatures, thereby reducing the risk of fire and ensuring high thermal efficiency at low electric power.

In the silver-nano electronic-ink print heating element separation-type electric thermotherapy apparatus manufactured using the aforementioned method, the integral heating element of conventional heating bedding is divided into three parts. Accordingly, heat emission from areas other than the area occupied by a user may be prevented to thus avoid excessive electric consumption.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The present invention may be applied to a heating mat including an integral heating element, such as an electric mat, an electric mattress, an electric cushion, a hot-water mat, and an electric carpet. The integral heating element includes two or more divided parts which are capable of being separately used.

The invention claimed is:

1. A silver-nano electronic-ink print heating element separation-type electric thermotherapy apparatus, comprising:
   silver-nano electronic-ink print heating elements that emit heat using a power source applied from a power source unit, each of the silver-nano electronic-ink print heating elements comprising:
      a substrate having a first surface and a second surface opposite to the first surface:
      a plurality of silver pastes each comprised of conductive silver ink, the plurality of silver pastes formed on the first surface of the substrate to form a pattern;
      a pair of electrodes formed on a pair of silver pastes among the plurality of silver pastes; and
      a positive temperature coefficient (PTC) ink printed on the substrate on which the plurality of silver pastes and the pair of electrodes are formed;
   a control unit which receives the power source from the power source unit to output a power source on-off signal and a temperature signal for controlling the silver-nano electronic-ink print heating elements,
   wherein the silver-nano electronic-ink print heating elements emit heat depending on the power source and a temperature applied using the control unit.

2. The silver-nano electronic-ink print heating element separation-type electric thermotherapy apparatus of claim 1, further comprising:
   an insulator having a first surface and a second surface, the first surface of the insulator facing the second surfaces of the substrates, the insulator formed on the second surfaces of the substrates;
   a lower outer cover comprising at least one of a polyethylene (PE) foam and a polyurethane (PI) foam, the lower outer cover formed on the second surface of the insulator;
   a blocking fabric formed on the positive temperature coefficient (PTC) inks an silver-nano nano electronic-ink print heating elements; and an upper outer cover formed on the blocking fabric.

3. The silver-nano electronic-ink print heating element separation-type electric thermotherapy apparatus of claim 2, wherein the blocking fabric comprises:
   a carbon non-woven fabric;
   a low density polyethylene (LDPE) film layer formed on the carbon non-woven fabric;
   a thermoplastic polyurethane (TPU) electromagnetic-wave blocking film layer laminated on the LDPE film layer.

4. The silver-nano electronic-ink print heating element separation-type electric thermotherapy apparatus of claim 1, further comprising:
   an insulator having a first surface and a second surface, the first surface of the insulator facing the second surfaces of the substrates, the insulator formed on the second surfaces of the substrates;
   a lower outer cover comprising at least one of a polyethylene (PE) foam and a polyurethane (PI) foam, the lower outer cover formed on the second surface of the insulator; and
   an upper outer cover laminated with a carbon non-woven fabric formed on the positive temperature coefficient (PTC) inks of the silver-nano electronic-ink print heating elements.

5. The silver-nano electronic-ink print heating element separation-type electric thermotherapy apparatus of claim 1, wherein the conductive silver ink includes a silver-nano gel and is manufactured so as to print the patterns through which an electric signal is applied.

6. The silver-nano electronic-ink print heating element separation-type electric thermotherapy apparatus of claim 1, wherein the PTC ink comprises one or more of a polymer, carbon, and graphite.

7. The silver-nano electronic-ink print heating element separation-type electric thermotherapy apparatus of claim 1, wherein the patterns are formed using a plate-making roller, which has an outer surface engraved with a core cell pattern and which includes the conductive silver ink injected into the core cell pattern, a pressing roller for pressing a film moving between the plate-making and pressing rollers to transfer a pattern of the plate-making roller on one side of the film using the conductive silver ink, and one or more guide rollers for guiding the film.

* * * * *